United States Patent
Ravier et al.

(10) Patent No.: US 10,045,531 B2
(45) Date of Patent: Aug. 14, 2018

(54) USE OF ONE OR MORE FATTY ACID ESTERS AS INSECTICIDE AND/OR ARACHNICIDE

(71) Applicant: Oleon NV, Evergem (Ertvelde) (BE)

(72) Inventors: Pierre Ravier, Compiegne (FR);
Matthieu Chatillon, Compiegne (FR);
Sebastien Barreau, Noyon (FR)

(73) Assignee: OLEON NV, Evergem (BE)

( * ) Notice: Subject to any disclaimer, the term of this patent is extended or adjusted under 35 U.S.C. 154(b) by 0 days.

(21) Appl. No.: 15/129,174

(22) PCT Filed: Mar. 24, 2015

(86) PCT No.: PCT/FR2015/050734
§ 371 (c)(1),
(2) Date: Sep. 26, 2016

(87) PCT Pub. No.: WO2015/145057
PCT Pub. Date: Oct. 1, 2015

(65) Prior Publication Data
US 2017/0094965 A1 Apr. 6, 2017

(30) Foreign Application Priority Data

Mar. 26, 2014 (FR) ...................... 1452607

(51) Int. Cl.
*A01N 37/02* (2006.01)
*A01N 25/04* (2006.01)
*C07C 69/22* (2006.01)

(52) U.S. Cl.
CPC ............. *A01N 37/02* (2013.01); *A01N 25/04* (2013.01); *C07C 69/22* (2013.01)

(58) Field of Classification Search
CPC combination set(s) only.
See application file for complete search history.

(56) References Cited

U.S. PATENT DOCUMENTS 4,147,800 A * 4/1979 Singer .................... A01N 31/02
514/546
4,698,222 A 10/1987 Grinda et al.
(Continued)

FOREIGN PATENT DOCUMENTS

DE 44 45 546 A1 6/1996
EP 0 242 581 A2 10/1987
(Continued)

OTHER PUBLICATIONS

Biosurf "Biotechnological Production Platform for new Tailor-made Glycolipid Biosurfactants" Jan. 1, 2009 [online]: Ghent University [retrieved on Jun. 12, 2017]. Retrieved from <www.biosurf.ugent.be/Biosurfactantia.htm>.*
(Continued)

*Primary Examiner* — Amanda L Aguirre
(74) *Attorney, Agent, or Firm* — Arent Fox LLP (57) ABSTRACT

The present invention relates to the use of one or more fatty acid esters, particularly 3-methylbutyl dodecanoate, or a mixture of fatty acid esters as insecticide and/or arachnicide and moreover relates to insecticide and/or arachnicide compositions containing same. The invention also relates to a method for controlling insects and/or arachnids.

22 Claims, 1 Drawing Sheet

(56) References Cited

U.S. PATENT DOCUMENTS

| | | | |
|---|---|---|---|
| 5,580,557 A | 12/1996 | Roberts | |
| 6,667,285 B1* | 12/2003 | Kawahara | C09K 5/045 252/68 |
| 2004/0116300 A1 | 6/2004 | Schnabel et al. | |
| 2012/0121737 A1 | 5/2012 | Vielhaber et al. | |
| 2013/0203842 A1 | 8/2013 | Newberry et al. | |

FOREIGN PATENT DOCUMENTS

| | | |
|---|---|---|
| EP | 0 839 448 A1 | 5/1998 |
| EP | 1 954 126 A0 | 6/2007 |
| FR | 2 377 154 A1 | 8/1978 |
| FR | 2 526 632 A1 | 11/1983 |
| WO | WO1996/19111 * | 6/1996 |
| WO | WO 96/22020 A1 | 7/1996 |

OTHER PUBLICATIONS

English Machine Translation of Reckmann et al. WO 96/19111 (dated Jun. 1996).*
International Search Report issued in International Patent Application No. PCT/FR2015/050734 dated Jun. 3, 2015 (3 pages).

* cited by examiner

USE OF ONE OR MORE FATTY ACID ESTERS AS INSECTICIDE AND/OR ARACHNICIDE

CROSS-REFERENCE TO RELATED APPLICATIONS

This application is a U.S. National Stage Application pursuant to 35 U.S.C. § 371 of International Patent Application PCT/FR2015/050734, filed on Mar. 24, 2015, and published as WO 2015/145057 on Oct. 1, 2015, which claims priority to French Patent Application 1452607, filed on Mar. 26, 2014, all of which are incorporated herein by reference in their entireties for all purposes.

The present invention relates to controlling insects and/or arachnids. It relates more particularly to the use of certain fatty acid esters and/or a mixture thereof as an insecticide and/or arachnicide and insecticide and/or arachnicide compositions (concentrates, solutions) containing same. The present invention also relates to a method for controlling insects and/or arachnids.

Insecticides and/or arachnicides are pharmaceutical or phytopharmaceutical products intended to control insects and/or arachnids respectively. Today, numerous insecticides and arachnicides exist, classified by chemical families which group together insecticides and/or arachnicides that have a similar mode of action. However, because of their mode of action, the majority of insecticide and/or arachnicide compounds available today have a not inconsiderable impact on the environment and/or health.

By way of example, the organochlorine compounds have the advantage of not being very toxic to humans. However, their high stability and their biodegradability to metabolite(s) that are even more stable have caused problems of accumulation in organisms and ecosystems, leading certain countries to ban their use.

Conversely, the organophosphorus compounds used extensively today have high toxicity but good biodegradability.

As for the pyrethroids, they have low toxicity to humans and are highly biodegradable. However, they appear to be toxic to certain aquatic organisms and to organisms beneficial to agriculture (such as bees). Furthermore, certain insects, such as pollen beetles, have developed resistance to pyrethroids.

In fact, in January 2013, the IRAC (Insecticide Resistance Action Committee) published the result of a study into pollen beetle resistance to pyrethroids. From this report, it emerges that only 7% of the pollen beetle population remains susceptible to pyrethroids.

Furthermore, this phenomenon of insecticide and/or arachnicide resistance is not a phenomenon limited to pollen beetles and to pyrethroids but, on the contrary, is a rapidly developing phenomenon which affects numerous types of insects and/or arachnids and different types of insecticides and/or arachnicides. This phenomenon of resistance developed by different insects and/or arachnids is also intensified by the repeated application of insecticides and/or arachnicides having the same mode of action. In order to avoid this phenomenon of resistance, strategies for applying insecticides and/or arachnicides are focused on alternating the modes of action and more recently, but in a limited manner, on combining them.

It results from the above that a need exists for new insecticides/arachnicides and/or combinations of insecticides and/or arachnicides having a reduced impact on the environment and human health and making it possible to have effective control of insects and/or arachnids, in particular while reducing the risk of developing resistance.

The work of the inventors has made it possible to demonstrate that certain fatty acid monoesters could advantageously be used as insecticide and/or arachnicide compounds.

Fatty acid monoesters can sometimes be used in pharmaceutical or phytopharmaceutical compositions as an adjuvant. By way of example, application EP 0839448 relates to a pesticide composition containing an active pesticide ingredient and 15 to 40% by weight of a fatty acid monoester. However, their use as an insecticide and/or arachnicide has never been described.

The present invention therefore relates to the use of a certain type of fatty acid esters as insecticide and/or arachnicide compounds. It relates more particularly to the use of a compound of formula (I) or a mixture of compounds of formula (I):

in which:
p is an integer comprised between 0 and 1,
q is an integer comprised between 0 and 3,
n is an integer comprised between 1 and 5, and
$R^1$ is an alkyl chain containing 7 to 13 carbon atoms,
as an insecticide and/or arachnicide.

It will be noted that in the context of the present application, and unless otherwise stipulated, the ranges of values indicated are to be understood as inclusive.

By "insecticide" is meant a substance intended to control insects in a preventive and/or curative manner.

By "control insects" is meant the act of killing adult insects, their larvae and/or their eggs, repelling them and/or controlling their proliferation. In particular, the compound of formula (I) or the mixture of compounds of formula (I) can be used not only as insecticides for agricultural use and/or for green spaces such as gardens, parks, but also as insecticides for human or veterinary use, in particular as repellents (such as "mosquito repellents").

Preferably, the compound of formula (I) or the mixture of compounds of formula (I) is used as an insecticide.

By "arachnicide" is meant a substance intended to control arachnids in a preventive and/or curative manner, and more particularly spiders and mites. Advantageously, the arachnicide is an acaricide.

By "control arachnids" is meant the act of killing adult arachnids, their larvae and/or their eggs, repelling them and/or controlling their proliferation. In particular, the compound of formula (I) or the mixture of compounds of formula (I) can be used not only as an arachnicide for agricultural use and/or for green spaces such as gardens, parks, but also as an arachnicide for human or veterinary use.

Preferably, R1 is an alkyl chain containing 7 to 13 carbon atoms, more preferably an alkyl chain containing 9 to 11 carbon atoms. By "alkyl chain" is meant more particularly an unsubstituted saturated linear alkyl chain.

The compounds of formula (I) and the mixtures of compounds of formula (I) have the property of being easily biodegradable and have a low toxicity towards both humans and animals, other than insects and arachnids.

According to a first embodiment, a compound of formula (I) or a mixture of compounds of formula (I) in which q=p=0 and optionally n=2 is used as an insecticide and/or arachnicide. More preferentially, they are isobutyl, isopentyl (or isoamyl) and isohexyl esters.

Even more preferentially, the compound of formula (I) is 3-methylbutyl dodecanoate (also known by the terms isoamyl laurate or isopentyl laurate).

This compound, which can originate from renewable resources, is completely and easily biodegradable, non-bioaccumulative and non-toxic to animals other than insects and arachnids. In particular, it is non-toxic to aquatic organisms and microorganisms. It is also non-toxic to humans and, additionally, does not present a risk of irritation of the skin and eyes. The compound is therefore safer and healthier for the famer using it, for the population living around the treated farm and for the environment in general. Furthermore, isoamyl laurate can advantageously originate from renewable resources. The use of this compound as an insecticide will therefore have a low impact on the environment.

According to a second embodiment, a compound of formula (I) or a mixture of compounds of formula (I) in which p=n=1 and q=3 is used as an insecticide and/or arachnicide. More preferentially, it is 2-ethylhexyl, preferably 2-ethylhexyl caprate and/or laurate.

As indicated above, the insecticide and/or arachnicide according to the invention has a low impact on the environment. Advantageously, the compound or the mixture of compounds of formula (I) originate from renewable resources and result for example from the esterification of palm-kernel oil and/or coconut oil by an alcohol of formula (II):

$$H_3C-(CH_2)_q-\overset{\overset{H}{|}}{\underset{\underset{CH_3}{|}}{\underset{(CH_2)_p}{C}}}-(CH_2)_n-OH \quad (II)$$

in which:
p is an integer comprised between 0 and 1,
q is an integer comprised between 0 and 3, and
n is an integer comprised between 1 and 5.

In general, coconut oil has the following saturated fatty chain composition: 5-9% C8; 5-10% C10; 44-53% C12; 13-19% C14; 8-11% C16; 1-3% C18, the percentages indicated being the percentages by weight with respect to the total weight of the composition and the figure following the letter C indicating the carbon number in the saturated fatty chain.

Similarly, in general, palm-kernel oil has the following saturated fatty chain composition: 2-5% C8; 2-4% C10; 45-56% C12; 13-18% C14; 6-12% C16; 1-3% C18.

According to a first embodiment, a compound of formula (II) in which q=p=0 and optionally n=2 is used as alcohol. Preferentially, they are isobutanol, isopentanol and isohexanol. More preferentially, the alcohol of formula (II) is 3-methylbutan-1-ol.

According to a second embodiment, 2-ethylhexan-1-ol or 2-methylbutan-1-ol is used as alcohol.

Preferably, the alcohol of formula (II) is a mixture containing approximately 80% 3-methylbutan-1-ol and approximately 20% 2-methylbutan-1-ol.

The insecticide and/or arachnicide compound or mixture of compounds according to the invention can be used as insecticides and/or arachnicides for agricultural use and/or for green spaces such as gardens, parks, or as insecticides and/or arachnicides for human or veterinary use.

Due to its complete harmlessness, the compound or mixture of compounds is entirely capable of being used as a repellent or "mosquito repellent" for human or veterinary use.

According to a preferred embodiment, such a repellent is in the form of a spray, the composition of which is intended to be sprayed into the air (aerosol dispenser), onto the skin or clothing. In this embodiment, the composition containing the compound or mixture of compounds is advantageously in the form of an emulsion.

According to another preferred embodiment, such a repellent is in the form of a diffuser, such as an essential oil diffuser, and electric diffuser or, more simply, a diffuser bracelet. In this embodiment, the composition containing the compound or mixture of compounds is advantageously in the form of a solid or oily concentrate.

Preferably, the insecticide and/or arachnicide compound or mixture is used as insecticides and/or arachnicides for agricultural use and/or for green spaces such as gardens, parks, in particular to treat, in a preventive or curative manner, insects of the family Hemiptera, Lepidoptera, Diptera and/or Coleoptera and/or arthropods of the family Acari.

Among the Hemiptera, the bird cherry-oat aphid (*Rhopalosiphum padi*), the common green shieldbug (*Nezara viridula*) and the tobacco whitefly (*Bemisia tabaci*) are more particularly targeted.

Among the Lepidoptera, the European corn borer (*Ostrinia nubilalis*), the pea pod borer (*Etiella zinckenella*), the noctuid moths (such as *Spodoptera frugiperda* and *exigua*), the gypsy moth (*Lymantria dispar*), the diamondback moth (*Plutella xylostella*) are more particularly targeted.

Among the Diptera, the wheat bulb fly (*Delia coarctata*) is more particularly targeted.

Among the Coleoptera, the pollen beetle (*Meligethes aeneus*), flea beetles (cabbage, flax, corn, etc.) and the Colorado potato beetle (*Leptinotarsa decemlineata*) are more particularly targeted.

And finally, among the Acari, the two-spotted spider mites (*Tetranychus* sp.) are more particularly targeted.

The insecticide or arachnicide composition or mixture according to the invention can advantageously be used to treat, preventively or curatively, fruit, ornamental, cereal, kitchen garden and/or oleaginous crops.

By fruit crops are meant more particularly bushes and fruit trees such as currant bushes, strawberry plants, peach trees, pear trees, apple trees, melons.

By ornamental crops are meant more particularly ornamental trees and bushes such as conifers, broadleaf trees, ornamental and/or flowering plants, ornamental fruit bushes and house plants. By way of example the following can be mentioned:
  as conifers: pines, spruces, larches, firs,
  as broadleaf trees: oaks, hornbeams, beeches, poplars, birches, willows, maples, limes, alders,
  as ornamental and/or flowering plants: cyclamens, dahlias, hortensias and rose bushes.

By "cereal crops", is meant more particularly corn, rice and straw cereals such as barley, oats, wheat, common wheat.

By "kitchen garden crops" is meant more particularly potatoes, aubergines, tomatoes, sweet peppers, certain cruciferae including cabbages and cauliflowers, carrots, squashes, cucumbers, green beans, beets and legumes such as peas, beans, lentils, broad beans.

Finally, by "oleaginous crops", is meant more particularly oilseed rape (or canola), cotton, sunflower, soya bean, flax and hemp.

More specifically, the insecticide and/or arachnicide compound or mixture according to the invention can advantageously be used to preventively or curatively treat:
among the fruit crops:
two-spotted spider mites (*Tetranychus* sp.) infesting or capable of infesting fruit bushes and trees such as currant bushes, strawberry plants, peach trees, pear trees and apple trees,
the European corn borer infesting or capable of infesting melon crops;
among the ornamental crops:
the tobacco whitefly (*Bemisia tabaci*) infesting or capable of infesting ornamental trees and bushes, house plants and rose bushes,
two-spotted spider mites (*Tetranychus* sp.) infesting or capable of infesting conifers, ornamental plants (such as cyclamens, dahlias and hortensias) and house plants,
the gypsy moth (*Lymantria dispar*) infesting or capable of infesting broadleaf trees such as oaks, hornbeams, beeches, poplars, birches, willows, maples, limes, alders, and conifers such as pines, spruces, larches and firs,
the beet armyworm (*Spodoptera exigua*) infesting or capable of infesting plants in greenhouses, pot plants, such as chrysanthemums, gerberas, rose bushes;
among the kitchen garden crops:
the Colorado potato beetle (*Leptinotarsa decemlineata*) infesting or capable of infesting crops such as those of potatoes, aubergines, tomatoes,
two-spotted spider mites (*Tetranychus* sp.) infesting or capable of infesting crops such as those of potatoes, aubergines, tomatoes, carrots, squashes, cucumbers, peas,
the tobacco whitefly (*Bemisia tabaci*) infesting or capable of infesting crops such as those of tomatoes, green beans,
the diamondback moth (*Plutella xylostella*) infesting or capable of infesting cabbage and cauliflower crops,
the common green shieldbug (*Nezara viridula*) infesting or capable of infesting crops such as those of aubergines, cucumbers, tomatoes, sweet peppers and beans,
the pea pod borer (*Etiella zinckenella*) infesting or capable of infesting legume crops such as peas, beans and lentils,
the flea beetle infesting or capable of infesting crops such as those of cabbages,
the beet armyworm (*Spodoptera exigua*) infesting or capable of infesting beet, sweet pepper crops;
among the cereal crops:
the wheat bulb fly (*Delia coarctata*) infesting or capable of infesting every kind of cereal,
the bird cherry-oat aphid (*Rhopalosiphum padi*) infesting or capable of infesting rice and straw cereals such as barley, oats, wheat, common wheat,
the European corn borer (*Ostrinia nubilalis*) infesting or capable of infesting corn, sunflowers, hemp,
the fall armyworm (*Spodoptera frugiperda*) infesting or capable of infesting corn, rice, sorghum,
the common green shieldbug (*Nezara viridula*) infesting or capable of infesting rice,
the flea beetle infesting or capable of infesting corn;
among the oleaginous crops:
the pollen beetle (*Meligethes aeneus*) and the diamondback moth (*Plutella xylostella*) infesting or capable of infesting oilseed rape,
the fall armyworm (*Spodoptera frugiperda*) and the tobacco whitefly (*Bemisia tabaci*) infesting or capable of infesting cotton,
the common green shieldbug (*Nezara viridula*) and the pea pod borer (*Etiella zinckenella*) infesting or capable of infesting soya beans,
flea beetles infesting or capable of infesting flax, oilseed rape;

Preferably, the insecticide and/or arachnicide compound or mixture according to the invention is an insecticide compound or mixture. Preferentially, it is used to preventively or curatively treat the bird cherry-oat aphid, the pollen beetle, the European corn borer and/or the Colorado potato beetle.

The present invention also relates to compositions, in particular concentrates and solutions which can be used as insecticides and/or arachnicides.

A concentrate according to the invention contains an insecticide and/or arachnicide compound or a mixture of insecticide and/or arachnicide compounds, the compound or compounds being selected from the group constituted by the compounds of formula (I):

in which:
p is an integer comprised between 0 and 1,
q is an integer comprised between 0 and 3,
n is an integer comprised between 1 and 5, and
$R^1$ is an alkyl chain containing 7 to 13 carbon atoms.

Preferably, R1 is an alkyl chain containing 7 to 13 carbon atoms, more preferentially an alkyl chain containing 9 to 11 carbon atoms. By "alkyl chain" is meant more particularly an unsubstituted saturated linear alkyl chain.

According to a first embodiment, a compound of formula (I) or a mixture of compounds of formula (I) in which q=p=0 and optionally n=2 is used as an insecticide and/or arachnicide. More preferentially, they are isobutyl, isopentyl (or isoamyl) and isohexyl esters.

Even more preferentially, the compound of formula (I) is 3-methylbutyl dodecanoate.

According to a second embodiment, a compound of formula (I) or a mixture of compounds of formula (I) in which p=n=1 and q=3 is used as an insecticide and/or arachnicide. More preferentially, they are 2-ethylhexyl esters, preferably 2-ethylhexyl caprate and/or laurate.

By "concentrate" is meant more particularly a composition which does not contain water. By "does not contain water" is meant a concentrate in which the optional presence of water is only due to the presence of water in the optional components of the concentrate (no added water).

According to a preferred first embodiment, the invention relates to a concentrate containing an effective quantity of an insecticide and/or arachnicide compound of formula (I) or a mixture of insecticide and/or arachnicide compounds of formula (I), a surfactant and less than 20% by weight of a hydrocarbon-containing aromatic solvent, the percentage by weight being given with respect to the total weight of the concentrate.

By "effective quantity" is meant more particularly a quantity strictly greater than 10% by weight with respect to the total weight of the concentrate, preferably at least 11%, more preferentially at least 15%, even more preferentially at least 30%.

By "solvent" is meant a substance the main function of which is to dissolve, dilute or extract other substances without causing chemical modification of these substances and without itself being modified. As the concentrate does not contain water, water is not considered as a solvent within the meaning of the present invention.

By "hydrocarbon-containing aromatic solvent" is meant more particularly the alkylbenzenes (such as xylene and tetramethylbenzene), the alkylnaphthalenes (such as naphthalene, methylnaphthalene), diphenylethane, phenyl xylyl ethane and mixtures thereof.

Preferentially, the quantity of hydrocarbon-containing aromatic solvent is at maximum 19% by weight with respect to the total weight of concentrate, more preferentially, at maximum 15%, even more preferentially at maximum 10%. For example, the quantity of hydrocarbon-containing aromatic solvent can be 0%.

The concentrate according to the invention can contain one or several agriculturally acceptable or pharmaceutically acceptable ionic or non-ionic surfactant(s). Examples of particularly advantageous surfactants are biosourced surfactants and/or biosurfactants. The biosurfactants are surfactants synthesized by microorganisms. Preferentially, the biosurfactant is a glycolipid, a glycoside or derivatives thereof.

The surfactant can be added to the composition directly or via the addition of an adjuvant.

By "incorporated via the addition of an adjuvant" is meant that the adjuvant added to the composition consists of or contains the surfactant.

By "adjuvant" is meant a product or a preparation lacking pharmaceutical or phytopharmaceutical activity which, combined with a compound of formula (I) or a mixture of compounds of formula (I), improves the physical, chemical or biological qualities thereof, in particular their insecticide and/or arachnicide activity, while limiting the harmful effects and the impact on human beings, fauna and flora.

The increase in insecticide and/or arachnicide activity of the insecticides and/or arachnicides according to the invention can, for example, result in a better vectorization or a better targeting of the part to be treated and/or an improvement in the stability of the insecticides and/or arachnicides, for example, by protecting them from ultra-violet light.

By way of example, as an adjuvant consisting of or containing one or more surfactant(s) the following can be mentioned: an adjuvant based on methyl esters from vegetable oils or animal fats and in particular methyl esters from rapeseed oil with surfactant(s) such as Actirob B®, Radiamix® or Vegestar® marketed by Novance®, an adjuvant based on soya bean lecithin and propionic acid such as Li-700® marketed by Agridyne®, an adjuvant based on an ethoxylated fatty amine polymer and polysorbate 20 such as Surf 2000® marketed by Jouffray-Drillaud JD®, polysorbate 20 such as Tween® 20 marketed by Croda®, an adjuvant based on octylphenol octaglycol ether such as Agral® Maxx or Extravon® by Syngenta®, an adjuvant based on polyethoxylated nonylphenol such as Agral® 90 by Syngenta®, an adjuvant based on alkylphenol polyethelene glycol esters such as Emulsol®, Phyteurop®, an adjuvant based on alkylphenol (poly)oxyethylene such as Etaldyne Jardin by Scotts France or Rosemox® by Bayer® Cropscience France, an adjuvant based on polyether trisiloxane such as Break Thru® S 240 by Evonik®, an adjuvant based on a phosphate ester of polyoxyalkylated fatty alcohol, fatty acid and oleic acid methyl esters such as Dash® HC by BASF® Agro, an adjuvant based on ethoxylated triglycerides such as Cantor® by Vivagro and an adjuvant based on ethyl esters from oleic sunflower oil and surfactants such as TRS2® by SDP.

According to a particular embodiment, the adjuvant contains a mixture of fatty acid esters, in particular, methyl esters from rapeseed oil, and at least one surfactant, preferably ionic and non-ionic surfactant(s).

Advantageously, the concentrate is an emulsifiable concentrate.

Thus formulated, the concentrate according to the invention has the advantage of being an insecticide and/or arachnicide that is biodegradable, less toxic to the environment, optionally even capable of being used in organic agriculture.

According to a second preferred embodiment, the concentrate comprises an effective quantity of a compound of formula (I) or of a mixture of compounds of formula (I) and a surfactant with the exception of the salts of alkyl aryl sulphonic acid and alkyl biphenyl sulphonic acid.

Preferably, the surfactant is a biosourced surfactant such as an alkyl polyglycoside (APG) or an alkyl polypentoside (APP), or a biosurfactant such as a glycolipid, a glycoside or derivatives thereof.

By "effective quantity" is meant more particularly a quantity strictly greater than 10% by weight with respect to the total weight of the concentrate, preferentially at least 11%, more preferentially at least 15%, even more preferentially at least 30%.

The concentrates according to the invention can also contain a solvent. The solvent can be mineral or vegetable, solid (for example in order to obtain repellent tablets or self-emulsifiable compositions) or liquid, agriculturally acceptable or pharmaceutically acceptable.

Like the surfactant, the solvent can be incorporated into the composition alone or via the addition of an adjuvant.

By way of example, as an adjuvant containing a solvent, alone or in combination with other compounds, the following can be mentioned: an adjuvant based on methyl esters from vegetable oils or animal fats such as Actirob B®, Radiamix® or Vegestar® (methyl esters from rapeseed oil with surfactant(s)) marketed by Novance® or such as Radia® 7961 (methyl esters from rapeseed oil), Radia® 7064 (methyl esters from soya bean oil) or Radia® (ethyl esters from oleic sunflower oil) marketed by Oleon®, an adjuvant based on a phosphate ester of polyoxyalkylated fatty acid, fatty acid and oleic acid methyl esters such as Dash®, HC by BASF® Agro, an adjuvant based on isodecyl alcohol ethoxylate such as Trend® 90 marketed by DuPont®, an adjuvant based on terpene alcohol such as Heliosol® marketed by Action Pin® and an adjuvant based on ethyl esters from sunflower oil and surfactants such as TRS2® by SDP.

Preferably, the concentrates according to the invention contain an agriculturally acceptable or pharmaceutically acceptable adjuvant.

Advantageously, when the adjuvant is an agriculturally acceptable adjuvant, it can contain, in addition to a surfactant and/or an optional solvent, a protein and/or one or more agents such as an antifoaming agent, an antifreeze agent, a thickening agent, a wetting agent, a retaining agent, a sticking agent, an anti-drifting agent or a stabilizing agent.

The majority of these adjuvants are particularly useful when the concentrate is intended to be emulsified in water then sprayed.

By "wetting agent" is meant an adjuvant which lowers the surface tension of the water, thus allowing the droplet to spread over the target.

By "retaining agent" is meant an adjuvant that promotes the sprayed droplets remaining on the target at the moment of impact.

By "sticking agent" is meant an adjuvant enabling better adhesion of the droplets sprayed onto the area to be treated at the moment of impact.

By "anti-drifting agent" is meant an adjuvant making it possible to not promote the creation of droplets that are too fine (<100-150µ) so as to obtain greater precision in the targeting of the sprayed product by reducing to the maximum the losses into the environment or towards neighbouring crops.

According to a particular embodiment, the concentrate contains an insecticide and/or arachnicide compound of formula (I) or a mixture of insecticide and/or arachnicide compounds of formula (I), a mixture of methyl esters from rapeseed oil, and at least one surfactant. Such a concentrate can be used in agriculture.

An effective quantity of the insecticide and/or arachnicide compound of formula (I) or of the mixture of insecticide and/or arachnicide compounds of formula (I) is introduced into the concentrate, such as a quantity strictly greater than 10% by weight with respect to the total weight of the concentrate, preferentially at least 11%, more preferentially at least 15%, even more preferentially at least 30%.

Advantageously, the concentrate contains at least two ionic and non-ionic surfactants. The surfactants and a mixture of methyl esters from rapeseed oil are preferentially introduced into the concentrate via the addition of an adjuvant. By way of example, such an adjuvant advantageously contains from 50 to 99% by volume of methyl esters from rapeseed oil and 1 to 50% by volume of a mixture of ionic and non-ionic surfactants, the percentages by volume being given with respect to the total volume of the adjuvant. The adjuvant can be selected from Actirob B®, Radiamix® or Vegestar®.

Advantageously, the concentrates according to the invention contain a second insecticide and/or arachnicide compound, advantageously at a content from 1 to 100% by weight of the second insecticide and/or arachnicide compound with respect to the weight of the first insecticide and/or arachnicide compound, preferably from 10 to 50% by weight.

The second insecticide and/or arachnicide compound can be selected from the group constituted by: the pyrethrins and their derivatives, the pyrethroids, the organophosphorus compounds, the carbamates, the neonicotinoids, the anthranilam ides, the benzoyl ureas, the oxydiazines, the organochlorines, the phenylpyrazoles, the arylpyrroles, the avermectins, the spynosyns, growth regulators and juvenile hormone analogues.

The addition of a second insecticide and/or arachnicide to the concentrates according to the invention makes it possible to obtain an insecticide and/or arachnicide composition the insecticide and/or arachnicide activity of which is strengthened with regard to a particular insect and/or arachnid or of which the spectrum of insects and/or arachnids targeted is widened. Alternatively, it is also possible to reduce the content of the usual (potentially more toxic) or non-organic insecticide and/or arachnicide, thus making it possible to obtain an insecticide and/or arachnicide that is healthier or less toxic for the farmer, the vicinity of the fields treated and the environment. A combination of active insecticide and/or arachnicide ingredients also make it possible to reduce the resistance of the insects and/or arachnids to insecticides and/or arachnicides, using for example a combination of two insecticides and/or arachnicides having different modes of action. A person skilled in the art is familiar with the formulation of such insecticides and/or arachnicides.

By "pyrethrins and derivatives thereof" is meant more particularly Pyrethrins I and II (suitable for organic agriculture), Jasmolins I and II and Cinerins I and II.

By "pyrethroids" is meant more particularly the following active insecticide ingredients: Allethrin, d-Allethrin, Bioallethrin, Alphamethrin, Biphenthrin, Bioresmethrin, Cycloprothrin, Cyfluthrin, Beta-cyfluthrin, Cyhalothrin, Gamma-cyhalothrin, Lambda-cyhalothrin (org), d,d,trans-Cyphenothrin, Cypermethrin, Alpha-cypermethrin, Beta-cypermethrin, Zeta-cypermethrin, Cyphenothrin, Deltamethrin (org), Depallethrin, Dimefluthrin, Empenthrin, Esbiothrin, Esdepallethrine, Esfenvalerate, Etofenprox, Fenpropathrin, Fenvalerate, Flucythrinate, Fluvalinate, Tau-fluvalinate, Imiprothrin, Kadethrin, Metofluthrin, Permethrin, Phenothrin, D-Phenothrin (Sumithrin), Prallethrin, Profluthrin, Resmethrin, Silafluofen, Tefluthrin, Tetramethrin, D-Tetramethrin, Tralomethrin and Transfluthrin.

By "organophosphorus compounds" is meant more particularly the following active insecticide ingredients: Acephate, Azamethiphos, Azinphos-methyl, Bromofos-ethyl, Chlorfenvinphos, Chlorpyrifos, Chlorpyrifos-methyl, Coumaphos, Cyanophos, Demeton, Diazinon, Dichlofenthion, Dichlorvos, Dicrotophos, Dimethoate, Disulfoton, Ethion, Ethoprophos, Etrimfos, Fenchlorphos, Fenitrothion, Fenthion, Fonofos, Formothion, Heptenophos, lodofenphos, Isofenphos, Isoxathion, Malathion, Mecarbam, Methamidophos, Methidathion, Meniphos, Monocrotophos, Naled, Omethoate, Oxydemeton-methyl, Paraoxon, Parathion, Ethyl parathion, Methyl parathion, Phenthoate, Phosalone, Phosmet, Phosphamidon, Phorate, Phoxim, Pirimiphos-methyl, Pirimiphos-ethyl, Profenofos, Propetamphos, Prothiofos, Pyraclofos, Pyridaphenthion, Quinalphos, Sulfotep, Sulprophos, Tebupirimfos, Temephos, Terbufos, Tetrachlorvinphos, Thiometon, Triazophos, Trichlorfon and Vamidothion.

By "carbamates" is meant more particularly the following active insecticide ingredients: Alanycarb, Aldicarb, Aminocarb, Bendiocarb, Benfuracarb, Carbaryl, Carbofuran, Carbosulfan, Diallate, Dimetan, Dimetilan, Dioxacarb, Ethiofencarb, Fenobucarb (BPMC), Fenoxycarb, Formentanate, Formentanate hydrochloride, Furathiocarb, Isocarb, Isoprocarb (MIPC), Mercaptodimethur, Methiocarb, Methomyl, Metolcarb (MTMC), Mexacarbate, Oxamyl, Pirimicarb, Promecarb, Propoxur, Thiodicarb, Thiofanox and Triazamate.

By "neonicotinoids" is meant more particularly the active insecticide ingredients Acetamiprid, Clothianidin, Dinotefuran, Imidacloprid, Nitenpyram, Sulfoxaflor, Thiacloprid and Thiamethoxam.

By "anthranilamides" is meant more particularly the active insecticide ingredients Chlorantraniliprole and Cyantraniliprole.

By "benzoyl ureas" is meant more particularly the active insecticide ingredients: Chlorfluazuron, Diflubenzuron, Flucycloxuron, Flufenoxuron, Hexaflumuron, Lufenuron, Novaluron, Teflubenzuron and Triflumuron.

By "oxydiazines" is meant more particularly Indoxacarb.

By "organochlorines" is meant more particularly the following active insecticide ingredients Chlordane, DDT, Endosulfan, Lindane and Methoxychlor.

By "phenylpyrazoles" is meant more particularly the active insecticide ingredients Ethiprole and Fipronil.

By "arylpyrroles" is meant more particularly Chlorfenapyr.

By "avermectins" is meant more particularly the active insecticide ingredients Abamectin, Aversectin C, Doramectin, Emamectin, Eprinomectin, Ivermectin, Selamectin, preferably Abamectin, Aversectin C and Emamectin, more preferentially Abamectin.

By "spinosyns" is meant more particularly the active insecticide ingredients Spinetoram and Spinosad.

By "growth regulators" is meant more particularly the active insecticide ingredients Azadirachtin, Cyromazine and Dicyclanil.

By "juvenile hormone analogues" is meant more particularly the active insecticide ingredients, Hydroprene, Methoprene, S-Methoprene and Pyriproxyfen.

The compounds and active insecticide and/or arachnicide ingredients mentioned above can also be in the form of salt(s) (such as, for example, Emamectin benzoate) or in the form of a mixture of said compounds or salt(s) thereof.

The concentrates according to the invention can also contain a biopesticide, i.e. a pesticide substance of natural origin, a pesticide substance produced by plants containing plant incorporated protectants or a pesticidal microorganism.

By way of example the following can be mentioned:
bacteria such as *Bacillus thuringiensis* and/or the Bt toxin, *Bacillus subtilis*,
entomopathogenic fungi such as *Beauveria bassiana*, *Lecanicillium* spp., *Metarhizium* spp.,
insect pheromones, as well as any other substance emitted by an insect,
products originating from fermentation, such as for example the active insecticide ingredient Spinosad mentioned above,
chitosan,
minerals of natural origin such as sodium bicarbonate, diatomaceous earths, potassium silicate,
and more generally, any natural product derived from plants and/or plant extracts such as alkaloids, terpenoids, phenol derivatives, vegetable oils (rapeseed oil, neem oil), etc.

The concentrates can optionally contain a fertilizing product for plants such as a fertilizer (microorganisms, organic or mineral substances intended to provide plants with additional nutritional elements, in particular nitrogen, phosphorus, potassium, sulphur, magnesium and/or calcium), or an improver (compound or mineral intended to improve the quality of the soil).

They can also optionally contain another biologically active compound such as a nematicide and/or a bactericide.

The concentrate is advantageously in liquid form, gel form or solid form such as a powder, granules, a film, these formulations being preferentially emulsifiable or dispersible in water.

According to a particular embodiment, the concentrate consists of:
an insecticide and/or arachnicide compound of formula (I) or a mixture of insecticide and/or arachnicide compounds of formula (I),
one or more surfactant(s),
optionally, one or more solvent(s), on condition that if the concentrate contains one or more hydrocarbon-containing aromatic solvent(s), the content of hydrocarbon-containing aromatic solvent(s) is less than 20% by weight,
optionally one or more adjuvant(s),
optionally, one or more other insecticide and/or arachnicide compound(s), preferably a second insecticide and/or arachnicide compound.

According to another particular embodiment, the concentrate consists of:
an insecticide and/or arachnicide compound of formula (I) or a mixture of insecticide and/or arachnicide compounds of formula (I),
one or more surfactant(s), with the exception of the salts of alkyl aryl sulphonic acid and alkyl biphenyl sulphonic acid,
optionally one or more solvent(s),
optionally one or more adjuvant(s),
optionally, one or more other insecticide and/or arachnicide compound(s), preferably a second insecticide and/or arachnicide compound.

The preferred definitions, contents, surfactant(s), solvent(s), adjuvant and second insecticide compounds mentioned above are also applicable to these two particular embodiments.

It should be noted that the concentrations according to the invention differ from the concentrations suitable for use in the field of cosmetics in that they do not contain an emollient, such as mono-, di- or triglycerides.

According to a particular embodiment, in the concentrates according to the invention the insecticide and/or arachnicide compound(s) of formula (I) are such that $q=p=0$.

Preferably, in the concentrates according to the invention, the insecticide and/or arachnicide compound of formula (I) is 3-methylbutyl dodecanoate (isoamyl laurate). Trials made it possible to show that a concentrate containing isoamyl laurate had an insecticide activity similar to a commercial insecticide containing Lambda-cyhalothrin, while being less toxic, particularly from the point of view of aquatic toxicity and toxicity in humans (through inhalation, irritation of the skin and eyes).

The invention also relates to an insecticide and/or arachnicide solution containing a concentrate according to the invention and water and to a method for the preparation of the insecticide and/or arachnicide solution according to the invention, by emulsion, dispersion or dilution of a concentrate according to the invention.

Advantageously, the ratio by volume of the concentrate according to the invention to water is comprised between 1:400 and 1:20, preferably between 1:300 and 1:30, even more preferentially between 1:250 and 1:40.

The solution, ready for use, is advantageously in the form of an emulsion, a dispersion or a suspension.

Preferentially, the solution is in the form of a sprayable emulsion. Such a formulation allows a homogenous distribution of the active insecticide and/or arachnicide ingredients over the zone to be treated during the application.

Optionally, during the preparation of the solution, it is possible to add an extemporaneous adjuvant.

The concentrates and solution according to the invention are suitable for use as insecticides and/or arachnicides in a preventive or curative manner.

Finally, the invention relates to two methods for controlling insects and/or arachnids.

According to a first method, a plant or a part thereof is brought into contact with an effective dose of a compound of formula (I), a mixture of compounds of formula (I), a concentrate according to the invention, or a solution according to the invention.

By "plant" is meant any member of the kingdom "*Plantae*", regardless of the stage of development thereof, such as the seed, the bulb, the seedling or the adult plant. By part of the plant is meant more particularly the leaves, the stalks, the flowers, the fruits, the spikes, the buds, the roots, the tubers etc.

According to a second method for controlling insects and/or arachnids, the soil to be treated is brought into contact with an effective dose of a compound of formula (I), a mixture of compounds of formula (I), a concentrate according to the invention, or a solution according to the invention.

The treatments can be carried out preventively or curatively, preferably by spraying.

In general, an effective dose from 0.2 to 10 L/ha of a compound of formula (I) or a mixture of compounds of formula (I) is applied.

In particular, the methods according to the invention are more particularly adapted to treat plants and soils intended to receive plants for fruit, ornamental, cereal, market garden and or oleaginous crop farming as described above.

Preferentially, the above methods are methods for controlling insects. The insects to be treated are more particularly from the family Hemiptera, Lepidoptera, Diptera and/or Coleoptera and/or arthropods of the family Acari, as described above.

The invention will be better understood in view of the examples which follow given by way of illustration, with reference to the figures, which show respectively.

EXAMPLE 1

Compositions and the Preparation Thereof 1.a) A composition according to the invention is obtained by mixing 0.1 mL of an adjuvant Actirob B® (adjuvant containing methyl esters from rapeseed oil with ionic and non-ionic surfactants) with 0.9 mL of 3-methylbutyl dodecanoate (also known by the name isoamyl laurate). This mixture is stirred vigorously by hand for 30 seconds, then for 30 seconds in a Vortex mixer. The mixture is then emulsified in water immediately prior to use.

1.b) A composition according to the invention is obtained by mixing 0.1 mL of an adjuvant Actirob B® with 0.9 mL of 2-ethylhexyl caprate according to the method described in 1.a).

1.c) By way of comparison, a composition is obtained by mixing 0.1 mL of an adjuvant Actirob B® with 0.9 mL of 2-ethylhexyl palmitate according to the method described in 1.a).

EXAMPLE 2

Efficacy on Aphids (*Rhopalosiphum padi*)

The trial was carried out on wheat infected with aphids.

Preparation of the Aphid Population

*Rhopalosiphum padi* aphids are reared on wheat in the laboratory. The rearing conditions are as follows: 14 hrs in the light at 18° C., and 10 hrs in darkness at 15° C. at a relative humidity (RH) of 60-70%.

Preparation of the Seedlings

"*Triticum aestivum*" wheat of the Apache variety is grown under the following conditions: 14 hrs in the light at 18° C., and 10 hrs in darkness at 15° C. at a relative humidity (RH) of 60-70%. For the experiments, seedlings having reached stage 12 on the BBCH-scale, i.e. 2 leaves, are chosen.

Experiment 2.a)

On D-1, 3 adult aphids are placed on each wheat seedling (approximately 30 seedlings per dose tested). The seedlings are kept for 14 hrs in the light at 18° C., and 10 hrs in darkness at 15° C. at a relative humidity (RH) of 60-70%.

On day D, the seedlings are treated with a composition as described in Example 1.a.). Emulsions containing the following doses of isoamyl laurate were tested: 1.35 L/ha (N/4), 2.7 L/ha (N/2), 5.7 L/ha (N), 10.8 L/ha (2N) and 16.2 L/ha (3N). Two controls are carried out: a first control using water and a second control using the adjuvant, tested alone, at a dose of 1.8 L/ha, which corresponds to the dose of adjuvant contained in dose 3N of isoamyl laurate. The volume of composition sprayed corresponds to the equivalent of 200 L/ha.

For the treatment, nozzles are used to spray the different emulsions and to produce a good distribution of the drops over the plants (TeeJet 100015-VS flat spray nozzle used on a Euro-Pulvé laboratory sprayer).

Results 2.a)

On D+1, D+3, D+7, the adults and larvae present on each seedling are counted.

Statistical analysis is carried out using XLSTATS and a variance analysis is carried out using a Newman-Keuls and a Dunnett's test. The Dunnett's tests used post hoc following an ANOVA give a probability of 0.00.

Figure 1:
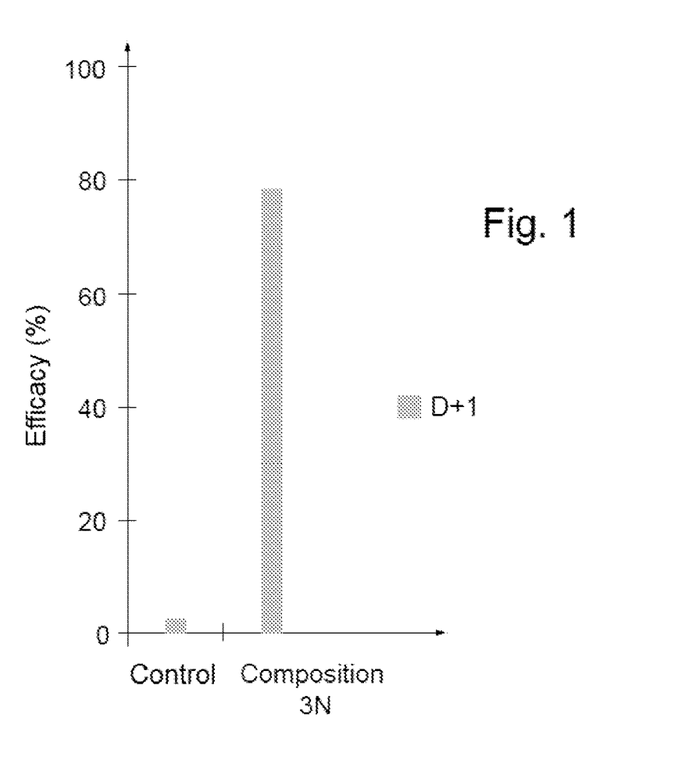
FIG. 1 shows a diagram illustrating the results of the insecticide efficacy of a composition containing only an adjuvant in comparison with those of a composition containing the same adjuvant with an insecticide product according to the invention.
Figure 2:
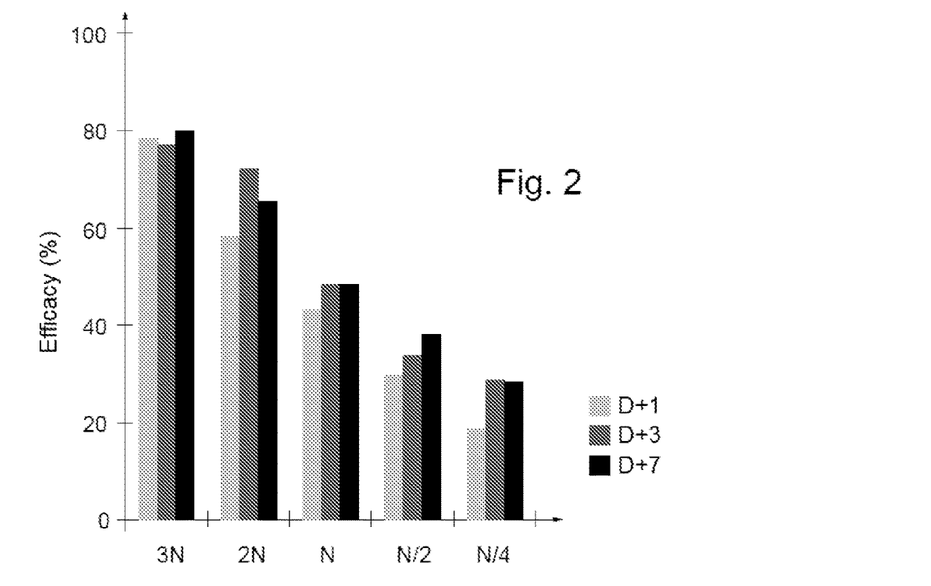
FIG. 2 shows a diagram illustrating the dose-response effect of the insecticide efficacy of a composition containing an insecticide product according to the invention at different doses.

The results are shown in FIGS. 1 and 2. In FIG. 1, the very limited insecticide effect of the adjuvant on the treatment of the seedling can be seen. Moreover, in FIG. 2, it can be seen that the isoamyl laurate has an efficacy of nearly 80% at dose 3N.

Experiment 2.b)

On D-1, 3 adult aphids are placed on each wheat seedling (approximately 30 seedlings per dose tested). The seedlings are kept for 14 hrs in the light at 18° C., and 10 hrs in darkness at 15° C. at a relative humidity (RH) of 60-70%.

The seedlings are treated on day D with a composition as described in Example 1.b). An emulsion containing the following dose of 2-ethylhexyl caprate was tested: 16.2 L/ha (3N). Two controls are carried out: a first control using water and a second control using the adjuvant, tested alone, at a dose of 1.8 L/ha, which corresponds to the dose of adjuvant contained in dose 3N of 2-ethylhexyl caprate. The volume of the composition sprayed corresponds to the equivalent of 200 L/ha.

For the treatment, nozzles are used to spray the different emulsions and to produce a good distribution of the drops over the plants (TeeJet 100015-VS flat spray nozzle used on a Euro-Pulvé laboratory sprayer).

Results 2.b)

On D+1, D+3, D+7, the adults and larvae present on each seedling are counted.

Statistical analysis is carried out using XLSTATS and a variance analysis is carried out using a Newman-Keuls and a Dunnett's test. The Dunnett's tests used post hoc following an ANOVA give a probability of 0.00.

The insecticide effect of the adjuvant is in this instance again very limited in treating the seedling. Moreover, it should be noted that the 2-ethylhexyl caprate has an efficacy of nearly 55% at the dose 3N on D+1.

Experiment 2.c)

On D-1, 3 adult aphids are placed on each wheat seedling (approximately 30 seedlings per dose tested). The seedlings are kept for 14 hrs in the light at 18° C., and 10 hrs in darkness at 15° C. at a relative humidity (RH) of 60-70%.

The seedlings are treated on day D with a composition as described in Example 1.c). An emulsion containing the following dose of 2-ethylhexyl palmitate was tested: 16.2 L/ha (3N). Two controls are carried out: a first control with water and a second control with the adjuvant, tested alone, at a dose of 1.8 L/ha, which corresponds to the dose of the adjuvant contained in the dose 3N of 2-ethylhexyl palmitate. The volume of the composition sprayed corresponds to the equivalent of 200 L/ha.

For the treatment, nozzles are used to spray the different emulsions and to produce a good distribution of the drops over the plants (TeeJet 100015-VS flat spray nozzle used on a Euro-Pulvé laboratory sprayer).

Results 2.c)

On D+1, D+3, D+7, the adults and larvae present on each seedling are counted.

Statistical analysis is carried out using XLSTATS and a variance analysis is carried out using a Newman-Keuls and a Dunnett's test. The Dunnett's tests used post hoc following an ANOVA give a probability of 0.00.

The insecticide effect of the adjuvant is in this instance again very limited in treating the seedling. Moreover, it can be seen that the 2-ethylhexyl palmitate has an efficacy of approximately 10% at the dose 3N on D+1.

EXAMPLE 3

Efficacy on the European Corn Borer (*Ostrinia nubilalis*)

The test was carried out on corn infected by the European corn borer.

Preparation of the Moth Population

Egg clusters from *Ostrinia nubilalis* are kept under controlled laboratory conditions in order to allow the eggs to develop. The eggs are kept for 14 hrs in the light and at 18° C., and for 10 hrs in the dark at 15° C. at a relative humidity varying from 60 to 70%.

After emerging, the larvae at the 1st and 2nd instar stages are used in the experiment.

Preparation of the Seedlings

"*Zea Mays*" corn of the variety DK315 is grown under the following conditions: 14 hrs in the light at 18° C., and 10 hrs in darkness at 15° C. at a relative humidity (RH) of 60-70%.

Experiment

On D-1, 3 corn leaves are taken from the seedlings and placed in ventilated plastic boxes. 10 larvae are then placed onto the corn leaves in each box, the trial being repeated three times. The larvae are kept for 14 hrs in the light at 18° C., and 10 hrs in darkness at 15° C. at a relative humidity (RH) of 60-70%.

The leaves are treated on day D with a composition as described in Example 1.a) with a dose of isoamyl laurate equivalent to 6.0 L/ha.

For the treatment, nozzles are used to spray the composition in example 1.a) and to produce a good distribution of the drops onto the plants (TeeJet 110015-VS flat spray nozzle used on a Euro-Pulvé laboratory sprayer). The volume of the composition sprayed corresponds to the equivalent of 200 L/ha.

Results

On D+3, the larvae and adults present in each box are counted.

Statistical analysis is carried out using XLSTATS and a variance analysis is carried out using a Newman-Keuls and a Dunnett's test. The Dunnett's tests used post hoc following an ANOVA give a probability of 0.05.

At a dose of 6.0 L/ha of isoamyl laurate, 19.5% efficacy is obtained against the larvae and adults of the European corn borer.

EXAMPLE 4

Efficacy on Pollen Beetles

The efficacy of isoamyl laurate against pollen beetles has been evaluated according to a protocol based on IRAC (Insecticide Resistance Action Committee) method no.11, version 3, June 2009.

Preparation of the Pollen Beetle Population

Pollen beetles are collected from different locations in infested fields. They are then kept in ventilated plastic boxes, in the bottom of which a dry paper has been placed. A number of oilseed rape leaves as well as 2 to 3 oilseed rape in flower are added as a food source. As it is important that the pollen beetles are not subjected to excessive temperatures, to humid conditions or other sources of stress following collection, they are kept under the following conditions: 14 hrs in the light at 18° C., and 10 hrs in darkness at 15° C. at a relative humidity (RH) of 60-70%.

Preparation of the Solutions to be Tested

The isoamyl laurate product was solubilized in acetone. Each solution was then placed in a homogeneous manner on the inside of a glass phial 2 cm in diameter and 4 cm in height, until the acetone has completely evaporated. The quantity of insecticide provided by 0.5 mL of acetone solution is calculated in such a way that a unit of area of the phial is covered with the same quantity of insecticide as that carried by the same unit of area of a leaf belonging to a field having undergone a treatment at 200 L/ha.

Experiment 10 pollen beetles are introduced into each phial, each trial being carried out twice.

Mortality is evaluated after 24 hrs.

Results

Table 1 below shows the efficacy obtained according to the dose tested after 24 hrs.

TABLE 1

| | | Efficacy (%) Pollen beetles *Meligethes aeneus* | |
|---|---|---|---|
| Product | Dose L/ha | Susceptible | Strains resistant to pyrethroids |
| Isoamyl laurate | 2.0 L/ha | 55% | 40% |
| | 4.0 L/ha | 90% | 75% |

EXAMPLE 5

Efficacy on the Colorado Potato Beetle
(*Leptinotarsa decemlineata*)

The efficacy of isoamyl laurate on Colorado potato beetles has been evaluated according to a protocol based on IRAC (Insecticide Resistance Action Committee) method no.7, version 3, June 2009.

Preparation of the Colorado Potato Beetle Population

Eggs from the Colorado potato beetle are collected from fields and placed on the lower (abaxial) surface of potato leaves. After 4 to 15 days, the hatching of the eggs takes place, producing dark red-brown larvae.

Preparation and Treatment of the Potato Leaves

Potato leaves are treated by soaking for 5 seconds in a composition as described in Example 1.a) at a dose of isoamyl laurate equivalent to 6.0 L/ha.

Experiment

The potato leaves are infested on the abaxial face thereof with 5 Colorado potato beetle larvae at stage L4. Each trial is repeated a second time.

Results

Mortality is evaluated after 5 hrs. At a dose of 6.0 L/ha of isoamyl laurate, 10% efficacy is obtained on the Colorado potato beetle larvae.

The invention claimed is:

1. A method for controlling insects and/or arachnids comprising contacting a plant or a part thereof or soil with an effective dose of 3-methylbutyl dodecanoate.

2. The method according to claim 1, wherein said insects are from the family Hemiptera, Lepidoptera, Diptera and/or Coleoptera and/or arthropods from the family Acari.

3. The method according to claim 1, comprising contacting fruit, ornamental, cereal, kitchen garden or oleaginous crops.

4. The method according to claim 1, wherein the soil is infested is with insects and/or arachnids.

5. A method for controlling insects and/or arachnids comprising contacting a plant or a part thereof or soil with an effective dose of a concentrate comprising 3-methylbutyl dodecanoate, a surfactant and less than 20% by weight of a hydrocarbon-containing aromatic solvent.

6. The method according to claim 5, wherein the concentrate further comprises a second insecticide and/or arachnicide compound.

7. The method according to claim 5, wherein the soil is infested is with insects and/or arachnids.

8. A method for controlling insects and/or arachnids comprising contacting a plant or a part thereof or soil with an effective dose of a concentrate comprising 3-methylbutyl dodecanoate and a surfactant with the exception of the salts of alkyl aryl sulphonic acid and alkyl biphenyl sulphonic acid.

9. The method according to claim 8, in which the surfactant is a biosurfactant.

10. The method according to claim 8, wherein the soil is infested is with insects and/or arachnids.

11. A method for controlling insects and/or arachnids comprising contacting a plant or a part thereof or soil with an effective dose of a solution comprising a concentrate comprising 3-methylbutyl dodecanoate, a surfactant and less than 20% by weight of a hydrocarbon-containing aromatic solvent and water.

12. The method according to claim 11, wherein the solution is an emulsion, a dispersion or a dilution of the concentrate.

13. The method according to claim 11, wherein the soil is infested is with insects and/or arachnids.

14. A method for repelling insects and/or arachnids comprising spraying a compound of formula (I) or a mixture of compounds of formula (I) or a solution comprising a concentrate comprising a compound of formula (I) or a mixture of compounds of formula (I), a surfactant and less than 20% by weight of a hydrocarbon-containing aromatic solvent and water onto skin or clothing of a human, wherein formula (I) is in which:
p is an integer comprised between 0 and 1,
q is an integer comprised between 0 and 3,
n is an integer comprised between 1 and 5, and
$R^1$ is an alkyl chain containing 7 to 13 carbon atoms.

15. A method for controlling insects and/or arachnids comprising contacting a plant or a part thereof or soil with an effective dose of a compound of formula (I) or of a mixture of compounds of formula (I):

in which:
p is an integer comprised between 0 and 1,
q is an integer comprised between 0 and 3,
n is an integer comprised between 1 and 5, and
$R^1$ is an alkyl chain containing 7 to 13 carbon atoms,
wherein said compound of formula (I) or said mixture of compounds of formula (I) is the only active ingredient applied to said plant or a part thereof or soil.

16. The method according to claim 15, in which q=p=0 and optionally n=2.

17. The method according to claim 15, in which a compound of formula (I) is 3-methylbutyl dodecanoate.

18. The method according to claim 15, in which p=n=1, and q=3.

19. The method according to claim 15, in which $R^1$ is an alkyl chain containing 9 to 11 carbon atoms.

20. The method according to claim 15, wherein said insects are from the family Hemiptera, Lepidoptera, Diptera and/or Coleoptera and/or arthropods from the family Acari.

21. The method according to claim 15, comprising contacting fruit, ornamental, cereal, kitchen garden or oleaginous crops.

22. The method according to claim 15, wherein the soil is infested is with insects and/or arachnids.

* * * * *